United States Patent
Endou

(10) Patent No.: US 7,607,352 B2
(45) Date of Patent: Oct. 27, 2009

(54) ULTRASONIC SENSOR TRANSMITTING AND RECEIVING ULTRASONIC FREQUENCIES ADJUSTED ACCORDING TO TEMPERATURE

(75) Inventor: Noboru Endou, Okazaki (JP)

(73) Assignee: DENSO CORPORATION, Kariya (JP)

( * ) Notice: Subject to any disclaimer, the term of this patent is extended or adjusted under 35 U.S.C. 154(b) by 311 days.

(21) Appl. No.: 11/642,712

(22) Filed: Dec. 21, 2006

(65) Prior Publication Data

US 2007/0157728 A1  Jul. 12, 2007

(30) Foreign Application Priority Data

Jan. 6, 2006 (JP) ............... 2006-001827

(51) Int. Cl.
  *H01L 41/053* (2006.01)
(52) U.S. Cl. ............ 73/632; 310/315; 310/334
(58) Field of Classification Search ............ 73/632; 310/315, 334; 367/99
  See application file for complete search history.

(56) References Cited

U.S. PATENT DOCUMENTS 4,679,175 A * 7/1987 Eder et al. ............... 367/98
5,991,234 A * 11/1999 Sejalon et al. ............ 367/13
6,792,810 B2 * 9/2004 Kupfernagel et al. ..... 73/632
7,255,006 B2 * 8/2007 Spanke et al. ............ 73/587

FOREIGN PATENT DOCUMENTS

| JP | U-59-117979 | 8/1984 |
|----|-------------|--------|
| JP | A-62-15476  | 1/1987 |
| JP | A-4-54800   | 2/1992 |
| JP | A-6-289128  | 10/1994 |
| JP | A-8-237796  | 9/1996 |

\* cited by examiner

*Primary Examiner*—John E Chapman
(74) *Attorney, Agent, or Firm*—Posz Law Group, PLC

(57) ABSTRACT

Components of an ultrasonic sensor are contained in a cylindrical casing having an end wall closing one end of the casing. A vibrator such as a piezoelectric element is disposed in the casing in contact with the end wall. An integrated circuit chip that includes a signal generator, a filter device and a temperature sensor is contained in the casing. Vibrations generated in the vibrator are transferred to the end wall that transmits ultrasonic waves. Ultrasonic waves received by the end wall are converted into electrical signals in the vibrator. Frequency of the transmitting signals and a frequency region of the signals to be received are controlled according to the ambient temperature, so that they always coincide with a resonant frequency of the end wall which changes according to the ambient temperature. Thus, high transmitting/receiving efficiency is always realized, irrespective of the ambient temperature.

11 Claims, 2 Drawing Sheets

ULTRASONIC SENSOR TRANSMITTING AND RECEIVING ULTRASONIC FREQUENCIES ADJUSTED ACCORDING TO TEMPERATURE

CROSS-REFERENCE TO RELATED APPLICATION

This application is based upon and claims benefit of priority of Japanese Patent Application No. 2006-1827 filed on Jan. 6, 2006, the content of which is incorporated herein by reference.

BACKGROUND OF THE INVENTION

1. Field of the Invention

The present invention relates to an ultrasonic sensor transmitting and/or receiving ultrasonic waves having frequencies adjusted according to ambient temperature.

2. Description of Related Art

An example of an ultrasonic sensor is disclosed in JP-A-8-237796. The ultrasonic sensor includes a piezoelectric vibrator disposed in a cylindrical casing in contact with a thin end wall that closes one end of the cylindrical casing. In transmitting operation, the thin end wall vibrated by the piezoelectric vibrator transmits ultrasonic waves. In receiving operation, ultrasonic waves received by the thin end wall are transmitted to the piezoelectric vibrator and converted into electrical signals.

In order to obtain high efficiency, the thin end plate is vibrated at its resonant frequency by the piezoelectric vibrator. However, since a Young's modulus of the thin end wall changes according to ambient temperature, the resonant frequency also changes according to the ambient temperature. Therefore, there is a problem that the transmitting or receiving efficiency of the ultrasonic sensor decreases as the ambient temperature deviates from a standard temperature.

SUMMARY OF THE INVENTION

The present invention has been made in view of the above-mentioned problem, and an object of the present invention is to provide an improved ultrasonic sensor, efficiency of which is not adversely affected by the ambient temperature.

The ultrasonic sensor for transmitting ultrasonic waves is composed of a cylindrical casing having an end wall closing one end of the casing, a vibrator connected to the end wall, a signal generator for generating electrical signals to be supplied to the vibrator, and a temperature sensor for detecting ambient temperature of the casing. Electrical signals generated in the signal generator are supplied to the vibrator that converts the electrical signals into vibrations. The vibrations in the vibrator are supplied to the end wall that transmits ultrasonic waves.

It is most desirable to transmit signals having the same frequency as a resonant frequency of the end wall to obtain high transmission efficiency. However, the resonant frequency of the end wall changes according to its Young's modulus which changes according to the ambient temperature. According to the present invention, the frequency of the transmitting signals is adjusted according to the ambient temperature, so that the frequency coincides with the resonant frequency of the end wall. The cylindrical casing having the end wall may be made of a synthetic resin material, and the temperature sensor and the signal generator may be integrated into one chip.

The ultrasonic sensor according to the present invention may be used also as a receiver for receiving the ultrasonic waves. In this case, ultrasonic waves received by the end wall are converted into electrical signals that are fed to a filter device. The filter device selects only the electrical signals in a frequency region that coincides or includes the resonant frequency of the end wall. For this purpose, the frequency region is adjusted according to the ambient temperature. The ultrasonic sensor may be made to include both of the transmission function and the receiving function. In this case, the ultrasonic sensor may be mounted on an automotive vehicle to detect objects positioned in front of the vehicle. A bumper or a body of the vehicle may be used as a member for transmitting and receiving ultrasonic waves in place of the end wall of the cylindrical casing.

According to the present invention, the frequency of the transmitting and/or receiving signals is adjusted to coincide with the resonant frequency of the end wall that changes according to the ambient temperature. Therefore, high transmitting/receiving efficiency is always realized irrespective of the ambient temperature. Other objects and features of the present invention will become more readily apparent from a better understanding of the preferred embodiments described below with reference to the following drawings.

DETAILED DESCRIPTION OF THE PREFERRED EMBODIMENTS

Figure 1:
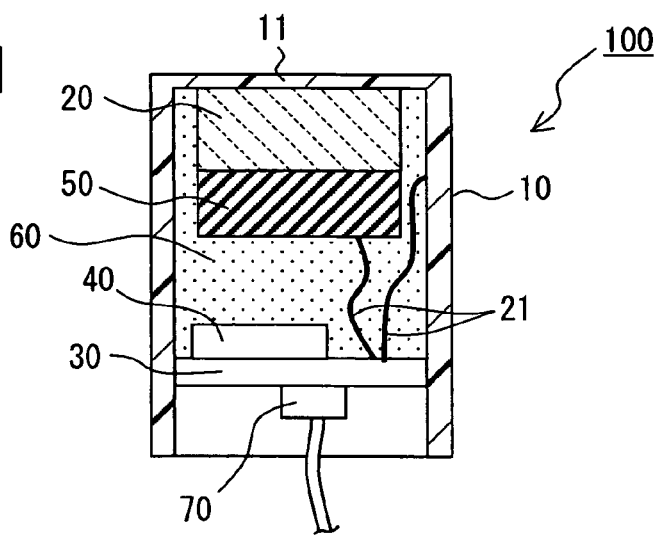
FIG. 1 is a cross-sectional view showing an ultrasonic sensor according to the present invention.

A first embodiment of the present invention will be described with reference to FIGS. 1 and 2. As shown in FIG. 1, an ultrasonic sensor 100 is composed of a cylindrical casing 10 with a thin end wall 11 closing one end of the casing, a vibrator 20, an absorbing member 50, a vibration-absorbing material 60, an IC-chip 40 mounted on a printed circuit board 30, and a connector 70. The printed circuit board 30 is electrically connected to the vibrator 20 through lead wires 21.

The cylindrical casing 10 is made of synthetic resin, for example. One end of the cylindrical casing 10 is closed with the thin end wall 11. The vibrator 20 is made of, e.g., piezoelectric ceramics such as sintered PZT or barium titanate. The vibrator 20 is connected to the thin end wall 11 with adhesive, and electrodes of the vibrator 20 are connected to the printed circuit board 30 through the lead wires 21. A conductive thin film is formed on an inner surface of the casing 10, and one of the lead wires 21 is connected to the thin film.

The IC-chip 40 (an Integrated Circuit chip) mounted on the printed circuit board 30 includes a signal generator for generating electrical signals to be fed to the vibrator 20 and a circuit for converting received ultrasonic waves into electrical signals. The IC-chip 40 will be described below in detail. The absorbing member 50 disposed in contact with the vibrator 20 and the vibration-absorbing material 60 filling the inside space of the cylindrical casing 10 absorb vibrations. Output signals of the ultrasonic sensor 100 are fed to an outside ECU (Electronic Control Unit) that includes a circuit for displaying information to a driver.

When the ultrasonic sensor 100 functions as a transmitter, the vibrator 20 is vibrated by electrical signals, and ultrasonic waves are transmitted from the end wall 11 contacting the vibrator 20. On the other hand, when the ultrasonic sensor 100 functions as a receiver, ultrasonic waves received by the end wall 11 is transferred to the vibrator 20, and the vibration of the vibrator 20 is converted into electric signals by piezoelectric effects. This means that the ultrasonic waves are transmitted or received via the end wall 11 in either case. In order to obtain high transmission or receiving efficiency, the end wall 11 has to be vibrated at its resonant frequency.

However, since the Young's modulus of the casing 10 changes according to the ambient temperature, the resonant frequency of the end wall also changes according to the ambient temperature. When the resonant frequency of the end wall deviates, the end wall cannot be vibrated at its resonant frequency even if electrical signals having a standard resonant frequency are fed to the vibrator. This means that the transmitting or receiving efficiency of the ultrasonic sensor 100 is decreased.

Figure 2:
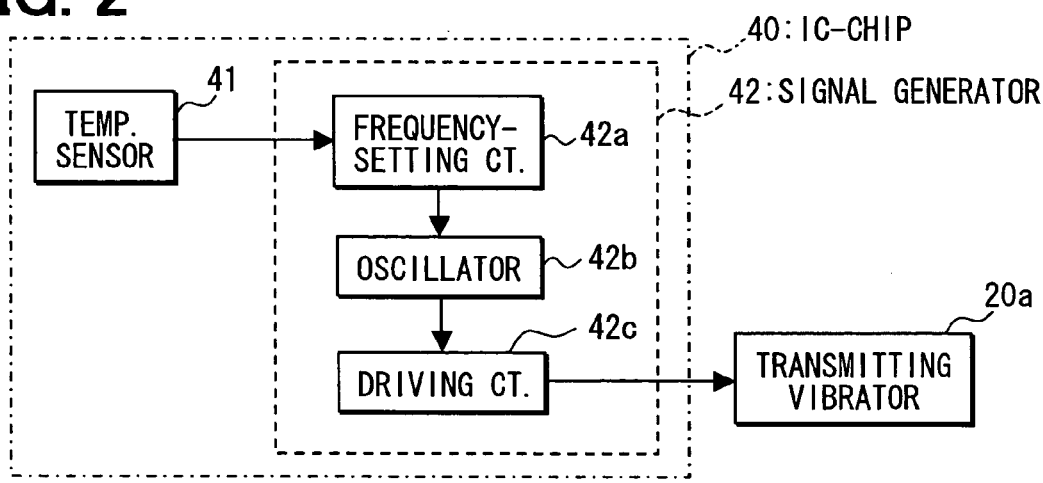
FIG. 2 is a block diagram showing electronic circuits in an ultrasonic sensor for transmitting ultrasonic waves, as a first embodiment of the present invention.

Referring to FIG. 2 that shows a first embodiment of the present invention, how the above-mentioned problem is solved will be described. In this embodiment, the IC-chip 40 is constituted so that the ultrasonic sensor 100 functions as a transmitter. The IC-chip 40 includes a temperature sensor 41 for detecting the ambient temperature and a signal generator 42 for vibrating a transmitting vibrator 20a at its resonant frequency that changes according to the ambient temperature.

The temperature sensor 41 is made of a temperature-sensitive resistor such as a dispersed resistor. In this particular embodiment, the dispersed resistor is formed by dispersing impurities on a semiconductor substrate. The dispersed resistor can be formed on a common substrate integrally with the signal generator 42, using known semiconductor processes. In place of the dispersed resistor, a carbon resistor formed on the substrate may be used.

The signal generator 42 is composed of a frequency-setting circuit 42a, an oscillator circuit 42b and a driving circuit 42c. The frequency-setting circuit 42a sets a frequency, at which the transmitting vibrator 20a is vibrated, based on the ambient temperature detected by the temperature sensor 41. The frequency is so set that it coincides with the resonant frequency of the end wall 11 which changes according to the ambient temperature. The oscillator 42b generates pulse signals having the frequency set by the frequency-setting circuit 42a, and the pulse signals are fed to a driving circuit 42c. The driving circuit 42c vibrates the transmitting vibrator 20a at the set frequency.

Since the end wall 11 of the casing 10 is always vibrated at its resonant frequency even if the resonant frequency is changed according to the ambient temperature, the transmitting efficiency of the ultrasonic sensor 100 is not adversely affected by changes in the ambient temperature. The casing 10 is made of a synthetic resin in this embodiment. An amount of changes in the Young's modulus of the synthetic resin according to the ambient temperature is higher than that of a metallic material. Namely, the resonant frequency of the synthetic resin changes more than that of the metallic material. Since the end wall 11 made of such synthetic resin is always vibrated at its resonant frequency according to the present invention, the transmitting efficiency of the ultrasonic sensor 100 can be kept at a high level, irrespective of the ambient temperature. In addition, the casing 10 can be manufactured at a lower cost with the synthetic resin than with a metallic material.

A second embodiment of the present invention will be described with reference to FIG. 3. In this embodiment, the IC-chip 40 is constituted so that the ultrasonic sensor 100 functions as a receiver. Ultrasonic waves received by a receiving vibrator 20b via the end wall 11 are amplified by an amplifier 43, and then amplified signals having a frequency set in a filter are taken out through the filter. Since the resonant frequency of the end wall 11 changes according to the ambient temperature, the resonant frequency may become different from the frequency set in the filter. In this case, output signals of the ultrasonic sensor 100 become lower than expected. Namely, the receiving efficiency of the ultrasonic sensor 100 decreases.

Figure 3:
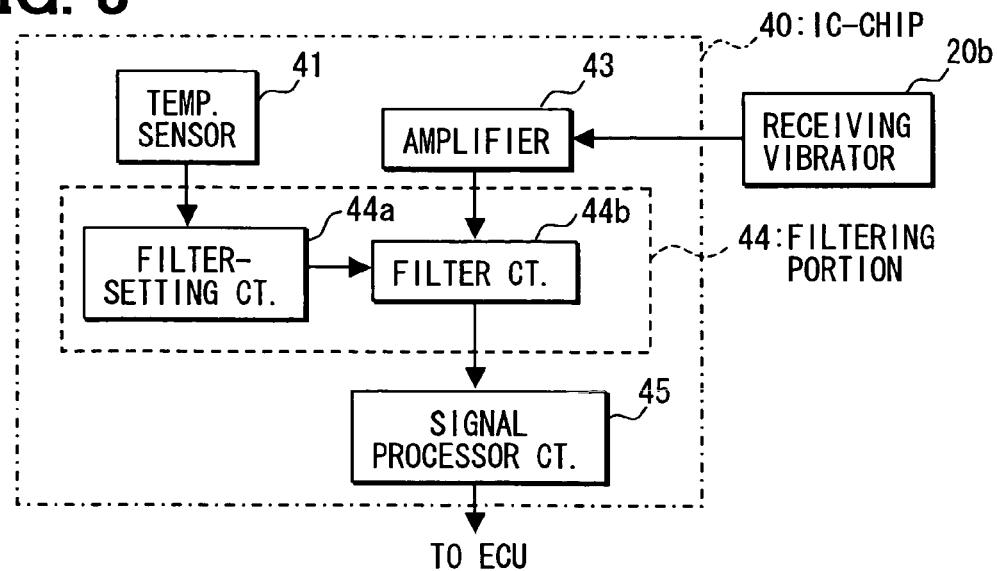
FIG. 3 is a block diagram showing electronic circuits in an ultrasonic sensor for receiving ultrasonic waves, as a second embodiment of the present invention.

This problem is overcome in the IC-chip 40 shown in FIG. 3. The IC-ship 40 includes a temperature sensor 41, an amplifier 43, a filtering portion 44 for selectively outputting signals having a frequency set in the filter, and a signal processor circuit 45. The same temperature sensor 41 as in the first embodiment is used in this second embodiment, too. The filtering portion 44 includes a filter-setting circuit 44a for setting a frequency to be filtered and a filter circuit 44b for outputting signals having the frequency set by the filter-setting circuit 44a. The filter-setting circuit 44a sets the frequency to be filtered based on the ambient temperature detected by the temperature sensor 41. The frequency (or a frequency region) to be filtered and outputted from the filtering portion 44 is set so that it coincides with (or includes) the resonant frequency of the end wall 11.

Since the frequency to be filtered and outputted from the filtering portion 44 is set to match the resonant frequency of the end wall 11 which changes according to the ambient temperature, the filter circuit 44b always outputs the signals having the resonant frequency of the end wall. Therefore, the receiving efficiency of the ultrasonic sensor 100 is not adversely affected by changes in the ambient temperature. The casing 10 is made of a synthetic resin material having high changes in Young's modulus as in the first embodiment to attain a low manufacturing cost. However, the receiving efficiency of the ultrasonic sensor 100 is not adversely affected by the changes in the ambient temperature because the frequency to be filtered and outputted from the filtering portion 44 is set to always coincide with the resonant frequency of the end wall 11.

Figure 4:
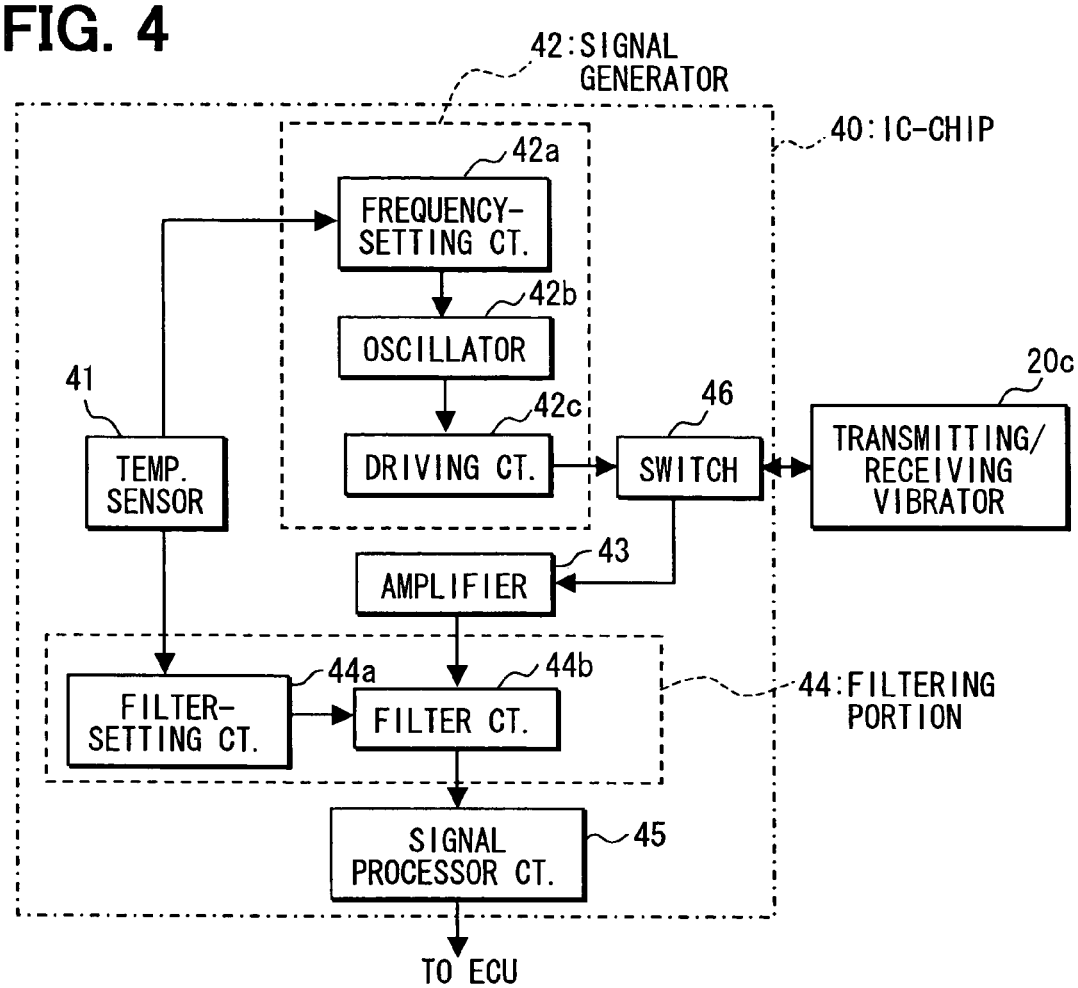
FIG. 4 is a block diagram showing electronic circuits in an ultrasonic sensor for transmitting and receiving ultrasonic waves, as a third embodiment of the present invention.

A third embodiment of the present invention will be described with reference to FIG. 4. In this embodiment, the ultrasonic sensor 100 is constituted to function as a transmitter and the receiver. Namely, the transmitter function in the first embodiment and the receiver function in the second embodiment are combined in the third embodiment. A common vibrator 20c functioning as the transmitting vibrator and the receiving vibrator is used in this embodiment.

The IC-chip 40 includes the temperature sensor 41 for detecting the ambient temperature, the signal generator 42 for generating signals to be transmitted, the amplifier 43, the filtering portion 44 and the signal processor 45. These components included in the IC-chip 40 are the same as those used in the first embodiment or in the second embodiment. The IC-chip 40 further includes a switch 46 for selecting either feeding of the signals generated in the signal generator 42 to the transmitting and receiving vibrator 20c or feeding of the signals received by the transmitting and receiving vibrator 20c to the amplifier 43. Received signals outputted from the filtering portion 44 are processed in the signal processor 45 and fed to the outside ECU.

The third embodiment structured as above operates in the following manner. In transmitting operation, the frequency-setting circuit 42a sets the frequency that matches the resonant frequency of the end wall 11 based on the ambient temperature. The oscillator 42b feeds pulse signals having the set frequency to the driving circuit 42c. The driving circuit 42c feeds driving signals to the transmitting and receiving vibrator 20c through the switch 46. The transmitting and receiving vibrator 20c vibrates at the resonant frequency of the end wall 11. Thus, the ultrasonic waves are sent out from the end wall 11.

In receiving operation, the filter-setting circuit 44a sets the frequency (or a frequency region) to be selected in the filter circuit 44b, based on the ambient temperature detected by the temperature sensor 41. The frequency to be selected is set to match the resonant frequency of the end wall 11 at a present ambient temperature. Signals received from the transmitting and receiving vibrator 20c are sent to the amplifier 43 through the switch 46. The filter circuit 44b selects the signals having the set frequency from the signals fed from the amplifier 43. The signal processor 45 processes the signals fed from the filtering portion 44 and sends the processed signals to the ECU.

The ultrasonic sensor described above as the third embodiment is advantageously used as a sensor for detecting a distance from a vehicle to an object positioned in front of the vehicle. The distance is calculated based on a period of time from sending out the ultrasonic waves to receiving the waves reflected by the object.

In the third embodiment, both of the transmitting efficiency and the receiving efficiency of the ultrasonic waves can be maintained at an optimum level, irrespective of the ambient temperature. Though the common vibrator 20c is used for transmitting and receiving the ultrasonic waves in the third embodiment, it is possible to use separate vibrators for respective operations. The ultrasonic sensor 100 can be made compact by using the common vibrator.

Figure 5:
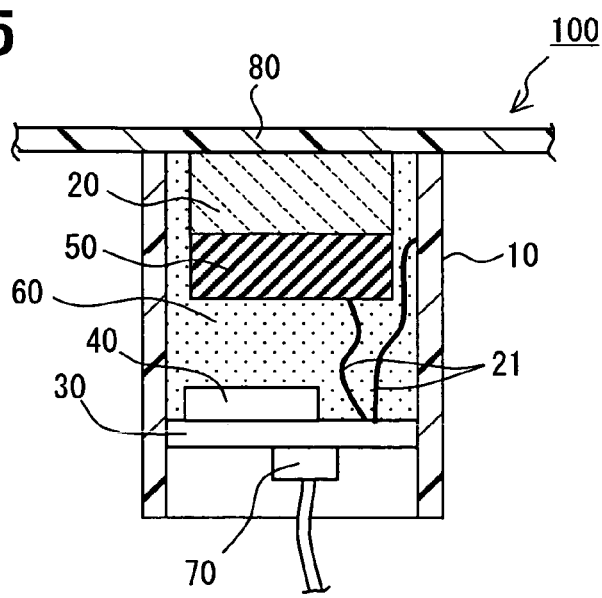
FIG. 5 is a cross-sectional view showing a modified form of the ultrasonic sensor.

The present invention is not limited to the embodiments described above, but it may be variously modified. For example, the casing 10 may be modified to a form shown in FIG. 5, and a resin bumper 80 of an automobile may be used, in place of the end wall 11, as a member for transmitting or receiving the ultrasonic waves. In this case, the vibrator 20 contained in the casing 10 is disposed in contact with the bumper 80. Similar effects as in the foregoing embodiments are attained in this modified form, too. Alternatively, the ultrasonic sensor 100 having the end wall 11 (the same sensors as in the foregoing embodiments) may be connected to the bumper 80 so that the end wall 11 closely contacts the bumper 80.

Though the temperature sensor 41 is included in the IC-chip 40 in the foregoing embodiments, the temperature sensor 41 may be separated from the IC-chip 40. A thermistor may be used as the temperature sensor. The circuits integrated in the IC-chip 40 may be separately mounted on the printed circuit board 30. Though the end wall 11 made of a resin material is used as the vibration-transmitting member in the foregoing embodiments, the vibration-transmitting member may be made of materials other than resin, such as aluminum or iron. Further, in place of the bumper 80 shown in FIG. 5, a body of an automobile may be used as the vibration-transmitting member.

While the present invention has been shown and described with reference to the foregoing preferred embodiments, it will be apparent to those skilled in the art that changes in form and detail may be made therein without departing from the scope of the invention as defined in the appended claims.

What is claimed is:

1. An ultrasonic sensor comprising:
   a receiving member for receiving ultrasonic waves;
   a vibrator for converting the ultrasonic waves to electrical signals;
   a filter device for selecting electrical signals in a predetermined frequency region from the electrical signals converted by the vibrator; and
   a temperature sensor for detecting ambient temperature of the receiving member, wherein:
   the predetermined frequency region is changed according the ambient temperature, so that the frequency region of the electrical signals selected by the filter device always includes a resonant frequency of the receiving member.

2. The ultrasonic sensor as in claim 1, wherein:
   the receiving member is an end wall closing one end of a cylindrical casing, and the vibrator is disposed in the casing in contact with the end wall.

3. An ultrasonic sensor comprising:
   a transmitting vibrator for converting transmitting electrical signals to transmitting vibrations;
   a receiving vibrator for converting receiving vibrations to receiving electrical signals;
   a signal generator for generating the transmitting electrical signals having a predetermined frequency to be supplied to the transmitting vibrator;
   a filter device for selecting electrical signals in a predetermined frequency region from the receiving electrical signals;
   a transmitting and receiving member for transmitting ultrasonic waves formed from the transmitting vibrations and for receiving ultrasonic waves to be supplied to the receiving vibrator; and
   a temperature sensor for detecting ambient temperature of the transmitting and receiving member, wherein:
   the predetermined frequency of the transmitting electrical signals is changed according to the ambient temperature, so that the frequency of the transmitting electrical signals coincides with a resonant frequency of the transmitting and receiving member; and
   the predetermined frequency region of the electrical signals selected by the filter device is changed according the ambient temperature, so that the frequency region always includes a resonant frequency of the transmitting and receiving member.

4. The ultrasonic sensor as in claim 3, wherein:
   the transmitting vibrator and the receiving vibrator are integrally formed as a single vibrator.

5. The ultrasonic sensor as in claim 4, wherein:
   the transmitting and receiving member is an end wall closing one end of a cylindrical casing, and the single vibrator is disposed in the casing in contact with the end wall.

6. The ultrasonic sensor as in claim 4, wherein:
   the transmitting and receiving member includes either a bumper or a body of an automobile.

7. The ultrasonic sensor as in claim 4, wherein:
   the transmitting and receiving member is made of a synthetic resin material.

8. The ultrasonic sensor as in claim 4, wherein:
   the temperature sensor is made of a temperature-sensitive resistor.

9. The ultrasonic sensor as in claim 8, wherein:
   the temperature-resistive resistor is made of a dispersed resistor formed on a substrate.

10. The ultrasonic sensor as in claim 4, wherein:
    the ultrasonic waves received by the ultrasonic sensor are ultrasonic waves transmitted from the ultrasonic sensor and reflected by an object positioned in front of a vehicle.

11. The ultrasonic sensor as in claim 3, wherein:
    the transmitting and receiving member is an end wall closing one end of a cylindrical casing, and the transmitting vibrator and the receiving vibrator are disposed in the casing in contact with the end wall.

* * * * *